(12) United States Patent
Arduini et al.

(10) Patent No.: US 8,992,508 B2
(45) Date of Patent: Mar. 31, 2015

(54) COUPLING DEVICE

(75) Inventors: Arduino Arduini, San Giovanni Teatino (IT); Paolo Cerasoli, San Giovanni Teatino (IT); Fabio Arrizza, San Giovanni Teatino (IT)

(73) Assignee: Glomeria Therapeutics SRL., San Giovanni Teatino, Chieti (IT)

( * ) Notice: Subject to any disclaimer, the term of this patent is extended or adjusted under 35 U.S.C. 154(b) by 1290 days.

(21) Appl. No.: 12/681,257

(22) PCT Filed: Oct. 2, 2008

(86) PCT No.: PCT/IB2008/054034
§ 371 (c)(1),
(2), (4) Date: Jul. 8, 2010

(87) PCT Pub. No.: WO2009/044364
PCT Pub. Date: Apr. 9, 2009

(65) Prior Publication Data
US 2010/0286625 A1    Nov. 11, 2010

(30) Foreign Application Priority Data
Oct. 2, 2007 (IT) .............................. RM2007A0512

(51) Int. Cl.
*A61M 39/00* (2006.01)
*A61M 39/10* (2006.01)
(52) U.S. Cl.
CPC ........... *A61M 39/10* (2013.01); *A61M 39/1011* (2013.01); *A61M 2039/1027* (2013.01); *A61M 2039/1083* (2013.01)

USPC ......................................... 604/533; 604/96.01
(58) Field of Classification Search
USPC ................. 604/533–284, 96.01, 164.01, 523, 604/174–180
See application file for complete search history.

(56) References Cited

U.S. PATENT DOCUMENTS 2,753,195 A * 7/1956 Palmer ..................... 137/614.03

FOREIGN PATENT DOCUMENTS

| EP | 1020203 A1 | 7/2000 |
|---|---|---|
| GB | 2060399 A | 5/1981 |
| WO | 89/10147 A1 | 11/1989 |

* cited by examiner

*Primary Examiner* — Kevin C Sirmons
*Assistant Examiner* — Phillip Gray
(74) *Attorney, Agent, or Firm* — Volpe and Koenig, P.C.

(57) ABSTRACT

A coupling device for connecting two ends of respective tubular members, allow the opening and the closing of a first tubular member and the simultaneous engagement of the two tubular members, as to prevent pollution, includes: a first case housing a first end of a respective first tubular member, comprising closing means of said first end; a second case, wherein a flexible terminal section of a respective second tubular member is received, comprising means for driving a second end of said second tubular member from a retracted position to a engagement position into said first end and vice versa; and means for reversibly connecting said first and second cases at a respective coupling port thereof, defining a single sealed environment; wherein the engagement and the disengagement of said second end and the automatic mechanical activation and deactivation of said closing means for opening and closing said first end.

11 Claims, 6 Drawing Sheets

COUPLING DEVICE

The present invention is related to a coupling device, in particular for the connection of the ends of respective tubular members, for establishing a continuity from one to another.

The invention is also related to the use of said device, specifically for the connection of a catheter, inserted within a living body, particularly a human body, to carry out, through said catheter and through the hose connected thereto, a treatment involving the extractions and/or the injection of fluids from/into the living body.

A specific embodiment is constituted by the joint of a catheter introduced inside a human body for implementing a transfusion.

A remarkable drawback in the known devices in that it is not prevented absolutely for sure the contact between the fluid flowing through the two hoses and through the connection thereof and even minimal surfaces, which have been previously exposed, for a very limited time too, to the open environment.

Such contact, how it is apparent, could imply a contamination of the fluid thwarting, in general terms, the purity and (or the complete asepticity of the fluid itself.

In particular, when one of the tubular members is a catheter, the contamination would lead to the extraneous, and possibly pathogenic, agent introduction inside the living body.

Another frequent problem is to determine the opening of the tubular member already inserted within the living body, exactly when the latter is connected to a second hose.

To an exemplificative purpose, when a central venous catheter (CVC) is adopted, the latter, when it is not used, is filled up with heparin to prevent the blood coagulation. The heparin is not mixed with the blood and is kept in its position by the blood pressure. When used, the catheter is connected to a second catheter and, first, the heparin is extracted. Then, washing solutions are used and the catheter is used for transfusions or for the administering of drugs, to be then emptied of the blood and filled up again with heparin.

Such steps, having a high level of complexity, require that the opening and the closing of the end of the catheter inserted within the living being occur very precisely and instantaneously, either when the heparin is extracted or when the blood plasma is introduced and so on.

In the medical practice, to prevent any contamination and the pollution of the hematic system, complex operations are required, executable by very skilled medical personnel. Where such skills are lacking, the connection operations cannot be carried out under conditions of clinical safety, substantially hindering the executions of medical treatments outside sanitary facilities.

The technical problems underlying the present invention is to provide a coupling device allowing to obviate to the drawback mentioned with reference to the known art.

Such a problem is solved by a coupling device for connecting two ends of respective tubular members, comprising:
- a first case housing a first end of a respective first tubular member, comprising closing means of said first end;
- a second case, wherein a flexible terminal section of a respective second tubular member is received, comprising means for driving a second end of said second tubular member from a retracted position to a engagement position into said first end and vice versa; and
- means for reversibly connecting said first and second cases at a respective coupling port thereof, defining a single sealed environment;

wherein the engagement and the disengagement of said second end and the automatic mechanical activation and deactivation of said closing means for opening and closing said first end.

An advantage of the device according to the present invention lies in allowing the contact of the flowing fluid only with parts kept inside a closed case, packaged and prepared with the due care in the specific field, and with the inner surfaces of the receiving tubular member end, thus excluding for sure any other surface. The coupling operation is inherently easy.

Further, through the connection step, the opening and the closing of the tubular member occur simultaneously with the engagement of the ends of the two tubular members, in such a way preventing any pollution.

Forming a tubular system without any staunching, possible blood coagulations are prevented.

The present invention will be disclosed hereinafter, according to some preferred embodiments thereof, given with an exemplificative and non-limitative purpose with reference to the annexed drawings wherein.

With reference to the figures, a coupling device is indicated by 1 as a whole. It is intended for the joint of a pair of tubular members at respective terminal ends thereof.

In the following, tubular members to be connected will be understood as flexible catheters, of the kind used in the clinical field. In the present embodiment, the coupling device or connector is used for joining the terminal ends of two catheters, e.g. for the carrying out of a transfusion, one of the two catheters being of the CVC kind. Therefore, the general features of the two catheters will be, in the present embodiment, the general features of catheters suitable to be used with living beings.

In particular, a first tubular member is composed by a first catheter 2 having a first terminal end 3 with an enlarged diameter, closed by a first cap 4. Such first end 3 will be identified hereinafter also with the term "receiving end". The cap 4 is intended to be fitted outside said end 3.

The coupling device 1, in the present embodiment, is intended to join a first catheter 2 with a second flexible catheter.

Therefore, the second catheter has a flexible terminal section 8 in turn comprising a respective second terminal end 9 to be connected to said first terminal end 3.

The device 1 comprises a first case 5 receiving said first end 3 of the first catheter 2. Such a case 5 has a substantially cylindrical shape, coaxial to the section of the catheter 2 passing through it longitudinally.

Such first case 5 has a distal end 6, wherein a port is formed, passed through by said first catheter 2, and a proximal end 7, wherein a coupling port is formed, placed at the terminal end 3 of the first catheter 2.

The first case 5 comprises and houses first closing means of said first end 3, indicated by 10 as a whole. Such closing means can be mechanically activated by means of interference with said second terminal end 9 of the second catheter.

In the present embodiment, such closing means comprises a tubular pipe 11, fitted on said first catheter 12 at the respective terminal end 3. The pipe 11 is completely received inside said first case 5. It has, in proximity of the terminal end 3, two opposed notches 12, leaving uncovered two facing areas of the catheter 2.

On the pipe 11, said closing means has a pliers device 12 formed by a locking ring 13, intended to be fitted and blocked on the pipe 11 at the distal end 6 of the first case 5, from which a pair of opposed claw clutches 14, each ending with an activation end 16 arranged at the port of said proximal end 7 of the first case 5.

The docking ring 13 is inserted by interference in a suitable locking seat 17, formed on the external surface of the pipe 11.

Each claw clutch 14 has further a tooth 15 which is inserted in the respective notch 12 of the pipe 11. Under normal conditions, the teeth 15 cooperate with each other for throttling and then closing the terminal end 3 of the catheter 2.

The claw clutches 14 are formed by resilient leaves, and a pressure on their activation ends according to a longitudinal direction toward the ring 13, i.e. toward the distal end 6 of the first case 5, can bend the claw clutches 14, moving away the teeth from each other and consequently opening the terminal end 3 of the catheter 2.

According to an alternative arrangement, the claw clutch could be a single one, possibly cooperating with a fixed stop, i.e. a tooth or a recess receiving the other tooth.

The clutch or the clutches may be also stiffened, hinged at an end thereof and rotated in response to a pressure exerted on the activation end.

Such rotation could occur in opposition to an elastic force, enough to keep the catheter dosed.

According to an alternative embodiment, the clutches may be replaced by a deformable pipe, pressed by resilient means, whose deformation results in a catheter throttling. Means can be provided to extend said pipe in combination with the coupling of the two catheters.

The device 1 then comprises a second case 20, wherein said flexible terminal section 8 of the respective second tubular member is received. The second end 9 is connected to a mobile coupling member 21, substantially ring shaped and internal to said second case 20.

Figure 1:
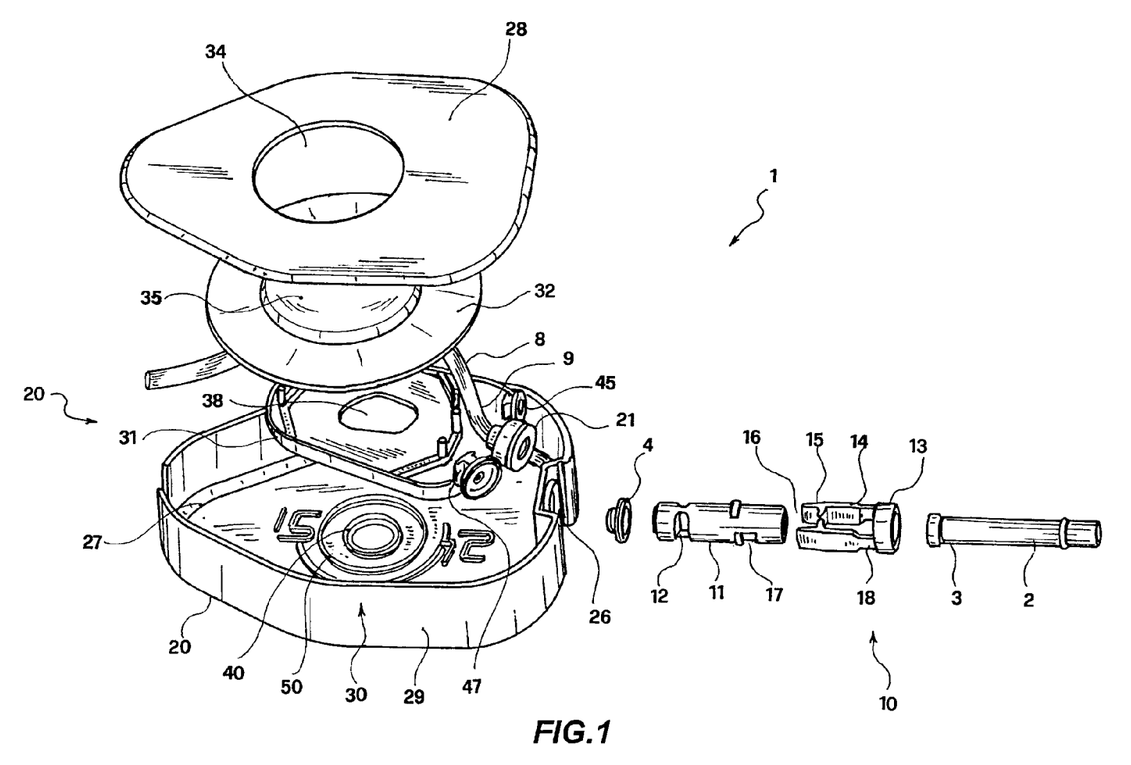
FIG. 1 shows a perspective and exploded view of a coupling device of a first embodiment according to the invention.
Figure 2:
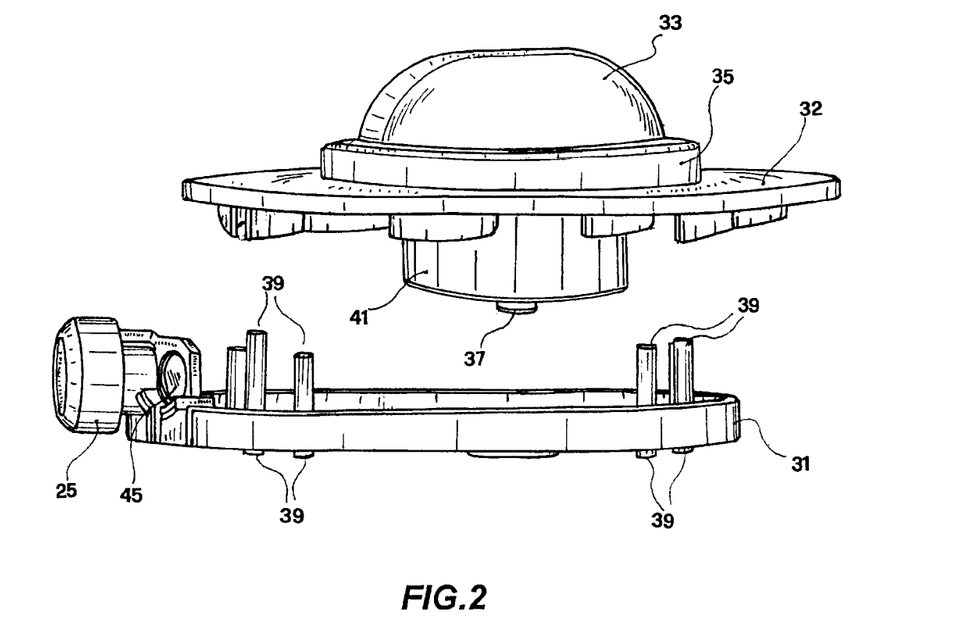
FIG. 2 shows a perspective view of some details of the coupling device of FIG. 1.
Figure 3:
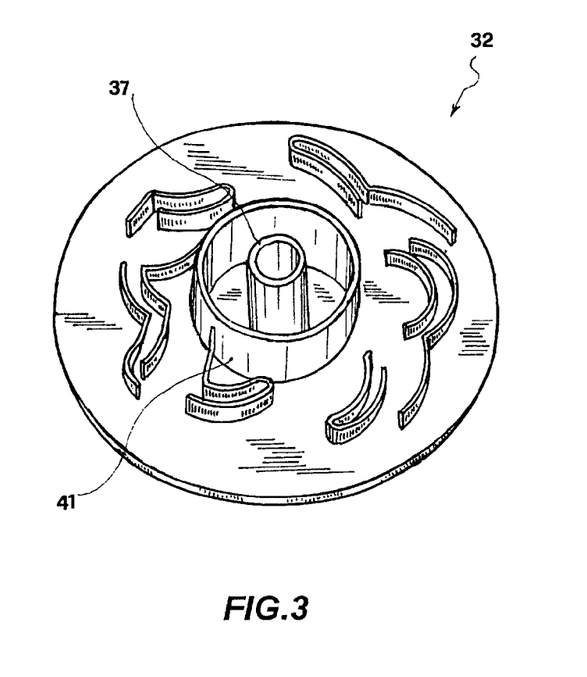
FIG. 3 shows a further perspective view of another detail of the coupling device of FIG. 1.
Figure 4:
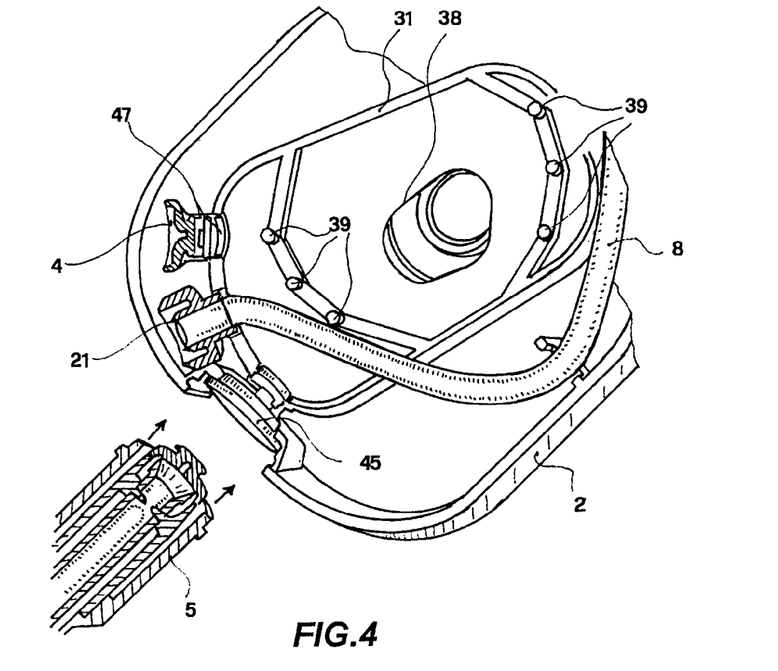
FIG. 4 shows a partial and sectioned perspective view of the device of FIG. 1 in a first working configuration.

The mobile coupling member 21 (FIG. 4, 4A) has a terminal bushing 22 with a tapered coupling edge 23, to ease the insertion thereof inside said first terminal end 3, and an activation extension 24, substantially cup-shaped, external and concentric to said terminal bushing 22, with an activation end 25 faced toward the terminal end 9.

The activation end 25 is arranged to interfere and to press the activation ends 16 of the claw clutches 14, in a way detailed in the following.

In is understood that the coupling member 21 can be provided with further and/or different means for mechanically deactivating the closing means 10 of the first catheter 2, e.g. pins or other members.

The second case 20 has then a respective second coupling port, indicated by 26, complementary to the coupling port formed at the proximal end 7 of the first case 5.

To carry out this coupling, the device 1 comprises means for reversibly coupling said first and second cases 5, 20 at the respective coupling ports thereof. Such coupling means can be of bayonet or threaded kind. The task thereof is to determine a single sealed environment, formed by said cases 5, 20, and to arrange in an appropriate position the first end 3 of the first tubular member 2, closed by the cap 4, and the activation ends 16 of the claw clutches 14 of the closing means 10 of said end 3.

The second case 20 is substantially boxed and flat shaped. It has a bottom wall 27 and a front wall 288, plane and parallel, connected by peripheral walls 29 in which the second coupling port 26 is formed.

Said second case 20 houses and comprises means for driving a second end 9 of said second tubular member, i.e. to drive the mobile coupling member 21 from a retracted position to a engagement position into said first end 3 of the first tubular member 2 and vice versa.

The engagement and the disengagement of said second end 9 causes the automatic mechanical activation, through the interference between the activation edge 25 and the activation ends 16, of said closing means 10 to close and open said first end 3.

As a matter of fact, theoretically the mobile coupling member 1 can race along circumferential r radial lines, or combinations thereof, with respect to a hinge pin of the second case 20.

Said means for driving, indicated by 30 as a whole, hence comprises a cam device intended to control the movement of said mobile coupling member which, to this purpose, is mounted on a mobile plate 31 having a plurality of projecting guide pins, generally indicated by 39 and perpendicularly extending toward said mobile plate 31, from both the opposed faces thereof.

The mobile plate 31, substantially parallel to the front and bottom walls 28, 27, is substantially rested on the latter and is, at the opposite face, trapped by a pivotable plate 32 from which a knob 33 projects extending form said front wall 28 through a suitable circular hole 34.

In particular, said knob 33 projects from a circular relief 35 arranged in a central position on the pivotable plate, so as to engage the whole area of the circular hole 34, and to determine an airtight closure, anyway allowing the rotation of the pivotable plate 32 with respect to the front wall 28, in response to a control imparted by said knob 33.

On the opposite face, the pivotable plate 32 has ribs 36 substantially forming a first cam profile in which the guide pins 39 of the mobile plate 31 are inserted, facing the pivotable plate 32.

Further, from this face of the pivotable plate 32, a cylindrical pins 37 projects, intended to pass through the mobile plate 31 at a central opening 38 thereof, and to be received in a pin seat 40 formed on said bottom wall 27. Further, from the same face an annular protrusion 41 projects, intended to be rested on said mobile plate 31 to press it and to keep it following the bottom wall 27.

On the latter wall, second cam profiles are formed by suitable grooves 50 in which the guide pins 39 of the mobile plate 31 are inserted.

The task of the cam profiles is therefore to drive the mobile plate 31, and then the coupling member 21 and the terminal end 9 of the second catheter for either engaging or disengaging with the first end 3 of the first catheter 2.

However, the mobile plate 31 can follow a complex path, being controller by a first cam profile, acting as true cam for the mobile plate 31 which represents the cam follower, and by a second cam profile acting as guide, substantially providing a desmodromic system, i.e. a double guide or a multiple guide.

In this connection, the mobile plate 31 not only controls said coupling member 21 but comprises cap catching means and cap releasing means.

Said catching and releasing means are substantially composed by cap seats formed in said mobile plate 31, or integral therewith, which will be described after in greater detail, placed at the sides of the coupling member 21, the latter being made integral with on a side of the mobile plate 31. Hence, it can roll to respectively bring the catching means, the coupling member and the releasing means in a position corresponding to the second coupling port 26 of the second case 20, i.e. at said first end 3 of the first catheter 2. Moreover, it can shift toward and from said end 3, for activating respectively the catching means, the coupling member and the releasing means.

In the present embodiment, the cap 4 is made of plastic material, e.g. a rubber, and has a recess wherein the end 3 of the first catheter 2 is received, surrounded by a rim 42 elastically interfering with the end 3 so as to seal it. It is noted however that the catheter is kept closed by said closing means 10.

From the opposite side, the cup 4 has a gripping projection 43, with circumferential elastic flaps 44.

Hence, the catching means comprise a first cap seat 45, substantially cup-shaped, wherein the gripping projection 43 is inserted. The elastic flaps 444 elastically interfere with the inner surface of the first cap seat 45 and, for geometrical interference, the gripping projection is caught into the seat 45.

To carry out the catch, it is sufficient to shift said seat 45 according to a direction coaxial to the cap 4 toward said first end 3, until the gripping projection 43 is inserted into the cap seat 45. Then, the first cap seat 45 is pulled back until the cap 4 is detached from the end 3 of the catheter 2.

Optionally, the first cap seat can have a circumferential tooth 46 apt to frame the elastic flaps 44 and the cap body, irreversibly catching the cap 4.

The releasing means is substantially equal to the catching means, it has a second cap seat 47 receiving a further cap, identical to the previously described one.

The second cap seat 47 keeps the respective cap 4 in the position thereof, but without interference between elastic flaps 44 and inner surface, as described for the first cap seat 45. To this purpose, the second cap seat 47 has a diameter slightly greater than the first seat and/or has the inner surface greased and/or antisticking, to ease the extraction of the gripping projection 43. In particular, such seat can be simply lacking in the circumferential tooth 46 described in relationship with the first seat 45. Therefore, it will be sufficient that the friction during the extraction step be less than that keeping the cap 4 in the receiving seat thereof.

To carry out the release, is then sufficient to shift said second seat 47 according to a direction coaxial to said first end 3, until the latter is inserted into the recess of the cap 4. Then, the second cap seat 47 is pulled back to detach the cap 4 therefrom.

As for the operation of this device, by check means (not shown) it is possible to impose a rotation direction to the pivotable plate 32, e.g. counterclockwise, to carry out the sequence of catching, engagement, disengagement, release. In this way, once the knob 33 is pivoted accordingly, the device 1, i.e. the portion thereof corresponding to to said second case 20, cannot be re-used keeping inside the used cap 4. Therefore, the device 1 can be classed as single-use and disposable device.

The device 1 is already provided with the flexible section 8 inside the second case 20, with the terminal end 9 thereof connected to the coupling member 21. It serves to connect, in the present embodiment, such section of a second catheter to a first catheter 2 which, to an exemplificative purpose, is a CVC catheter.

The so-obtained single tubular member shall be lacking in staunching.

The latter is already provided with the first case 5 and the coupling end 3 with enlarged diameter, closed by a cap 4 is throttled by the above described closing means.

Figure 4A:
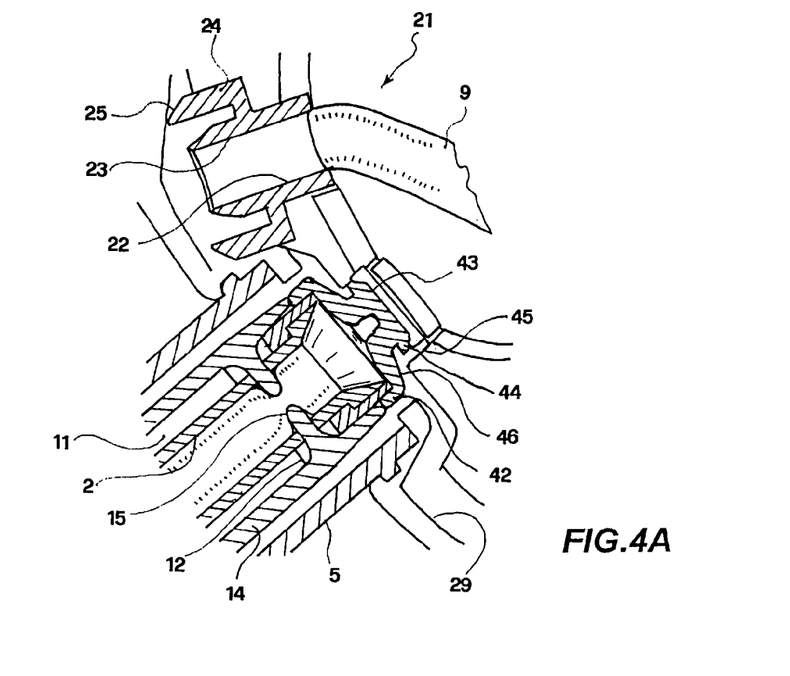
FIG. 4A shows an enlarged sectioned view of a detail of the device of FIG. 1 in a second working configuration.
Figure 5:
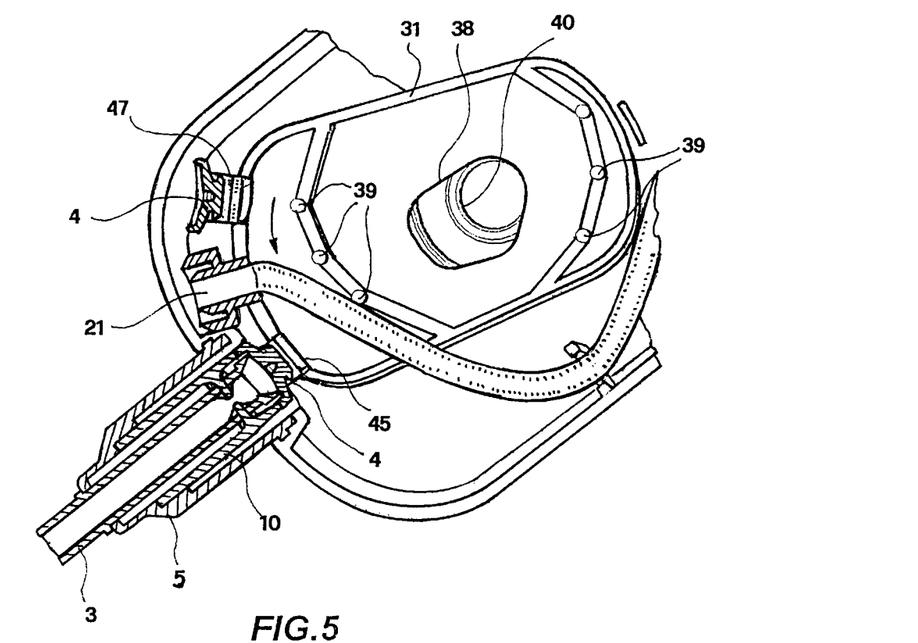
FIG. 5 shows the view of FIG. 4 with the device in a third working configuration.

The first and the second case 5, 20 are joined (FIG. 4) coupling the respective coupling ports and obtaining a closed and airtight enclosure, already housing the ends 3, 9 of the catheters to be coupled, on which it is possible to operate by controlling the knob 33. At the joint of the case 5 on the second case 20, the cap 4 is caught by the intended seat thereof (FIGS. 4A and 5).

The knob 33 is then pivoted from its starting position along a first angle, to a first position. This and the subsequent working positions of the knob 33 will be indicated by suitable marks outside the second case 20, and snap systems may be provided between the front wall 28 of the second case 20 and the pivotable plate 32.

Figure 8:
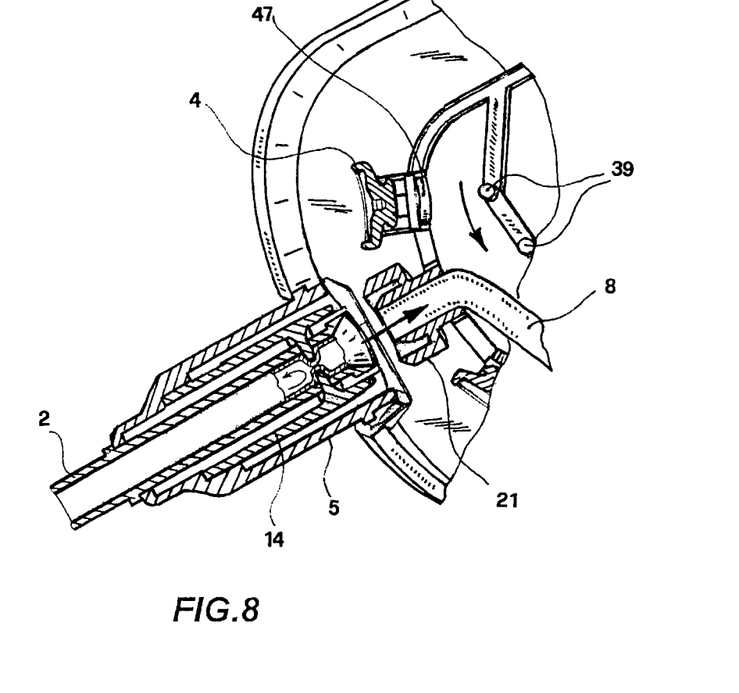
FIG. 8 shows the view of FIG. 7A with the device in a seventh working configuration.

The seat 45 is pulled back, (FIG. 8), keeping away the cap 4, leaving uncovered the end 3 of the catheter 2, however dosed by the closing means of the first case 5.

Figure 7A:
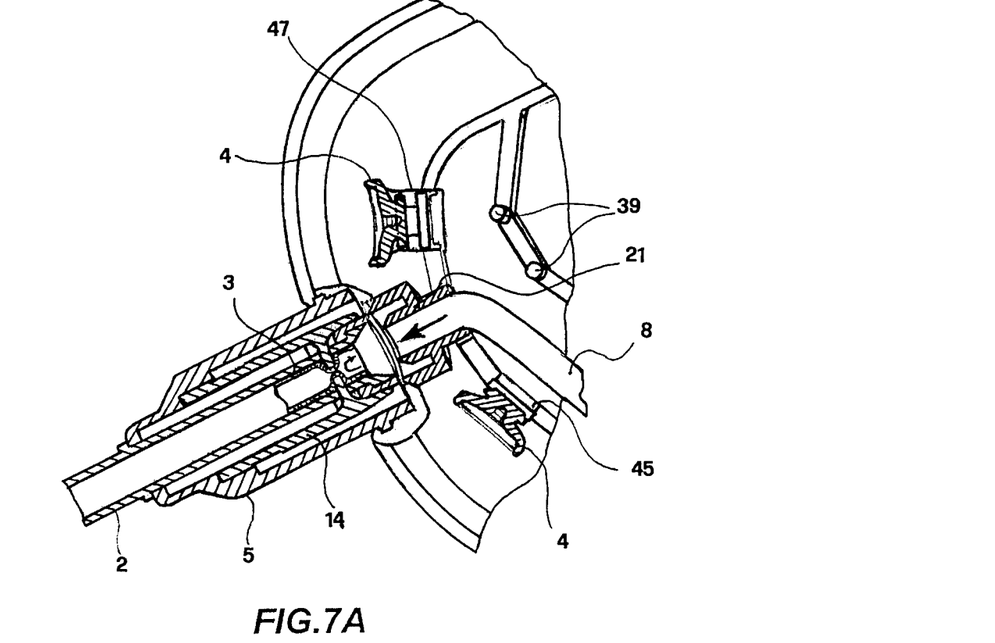
FIGS. 7A and 7B show a respective sectioned view of the device in a fifth and sixth working configuration.

Continuing to pivot the knob 33 and therefore the mobile plate 31 driven by the cam profiles on the pivotable plate 32 and on the bottom wall 27 of the second case 20, the coupling member 21 is first frontally placed at the coupling port 26 (FIG. 7A), and then is made put forth until the coupling edge 23 is inserted within the catheter 2 end, so as the activation edge 25 of the coupling member 21 press the activation ends 16 of the claw clutches, keeping away from each other the dosing teeth throttling the end 3 of the first catheter 2.

Figure 7B:
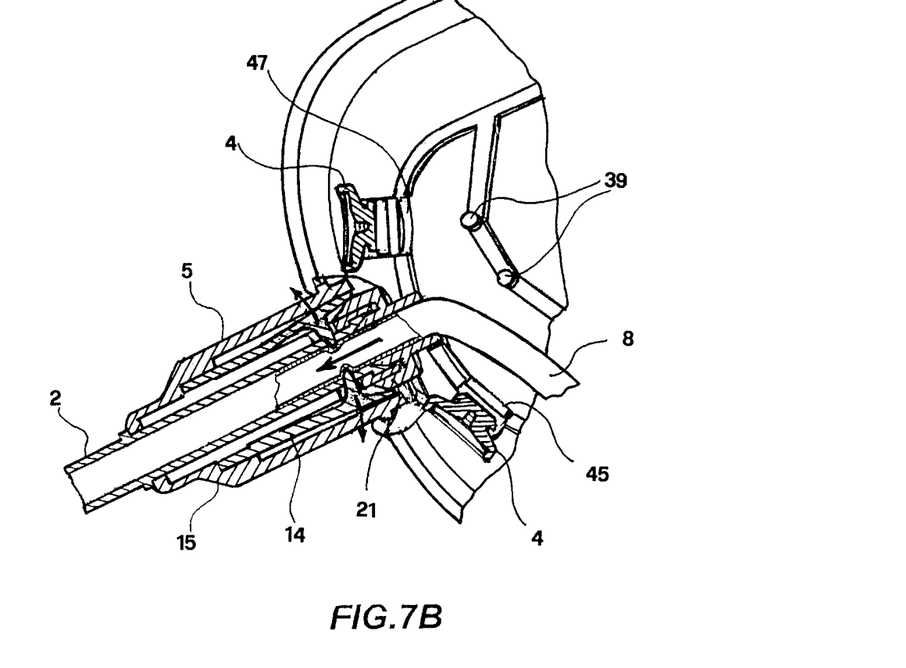

In this way, a fluid communication between the first and the second catheters is instantaneously carried out (FIG. 78).

Figure 6:
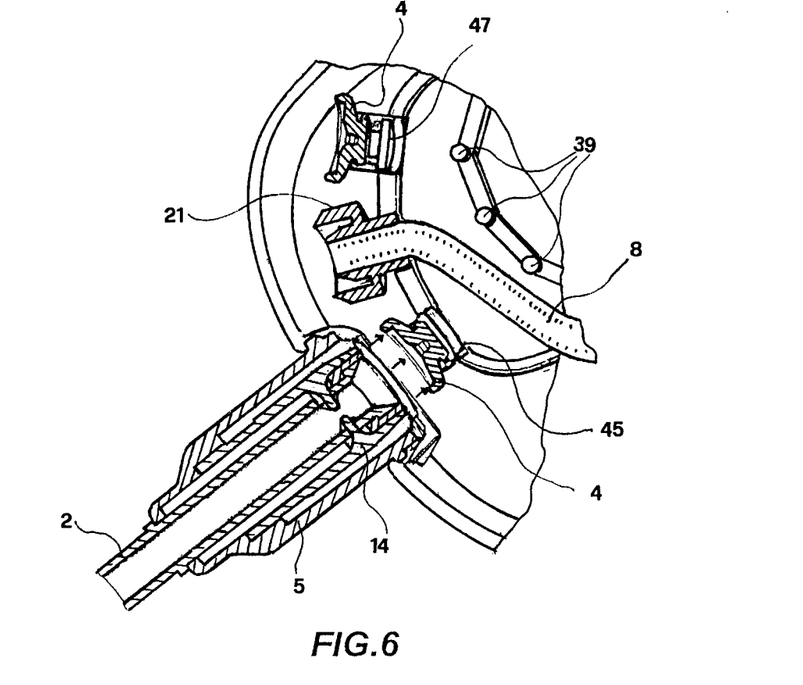
FIG. 6 shows the views of FIGS. 4 and 4A with the device in a fourth working configuration.

After having completed the step through which said coupling has been carried out, the knob 33 is pivoted, keeping the coupling member 21 away from the end 3 of the catheter 2. Therefore, the action of the activation edges 25 cease on the claw clutches 14, and the teeth 15 throttle back the catheter 2. Hence, the detachment between the coupling member 21 and the catheter 2 does not produce any fluid leaking from the first catheter 2 (FIG. 6).

The further pivoting of the knob 33 causes the rotation of the mobile plate 31 and then the coupling member 21 could be pressed against the surface of a fixed shutter (not shown), inside the peripheral wall 29 of the second case 20, thereby causing the closing of the second catheter too.

Figure 9:
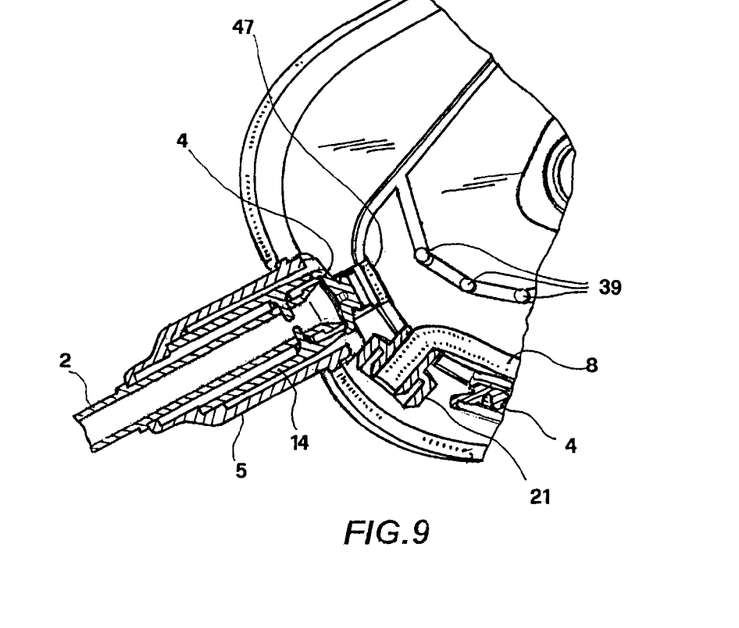
FIG. 9 shows a section of a more enlarged detail of the device of FIG. 1 in a eighth working configuration.

This rotation places the releasing means, i.e. the second cap seat 47 and the cap thereof, in front of said coupling port 26 of the second case 20. A further pivoting of the knob 33 causes the putting forth of the cap seat 47, until the cap 4 is fitted on the end 3 of the first catheter 2 (FIG. 9). Pivoting again the knob 33, the seat 47 is then pulled back, leaving the cap 4 closing the first catheter.

At this stage, it is possible to detach again first and second case 5, 20, leaving the first catheter 2 and the first case 5 thereof in a situation identical to that preceding the use of the device 1, whose second case 20 can be disposed and replaced with another kit, for the next use.

The consent to the detachment between the first and the second case 5, 40 can be mechanically provided by not shown stop means, preventing the detachment until the knob 33 is completely pivoted, just to avoid that an untimely detachment leave the end 3 of the first catheter 2 uncovered and disconnected.

However, it has to be noted that even in case of an untimely detachment, the closure means 10 are immediately re-activated, anyway closing the first catheter 2.

Therefore, it is understood that in the medical field, the device will be single-use and disposable, sold in a kit comprising a first catheter 2 with the respective first case 5 thereof, and a set of second catheters with the respective second cases 20 thereof.

According to the same principle, it is possible also to provide a coupling device wherein the second case receives also two sections of different catheters, or two coaxial catheters, then being provided two corresponding coupling members and a peculiar internal driving allowing the catch of the cap, the engagement and the disengagement with the first of said catheters, the possible release and the possible re-catch of an intermediate cap, the latter being completely optional steps, the engagement and the disengagement with a second of said second catheters, and the definitive release of a further cap, followed by the detachment of the two cases.

To the above disclosed coupling device a man skilled in the art, to meet further and contingent demands, can introduce several additional changes and variants, anyway all falling within the protection scope of the present invention, as defined by the annexed claims.

The invention claimed is:

1. Coupling device for connecting two ends of respective tubular members, comprising:
   a first case housing a first end of a respective first tubular member, comprising closing means of said first end;
   a second case, wherein a flexible terminal section of a respective second tubular member is received having a respective second end, comprising driving means to drive said second end of said second tubular member from a retracted position to an engagement position into said first end and vice versa, the driving means comprising a mobile plate to which said coupling member is connected and a cam device adapted to drive the movement of said mobile plate; and
   said first and second cases being reversibly connected at a respective coupling port thereof, defining a single sealed environment;
   the engagement and the disengagement of said second end causing the automatic mechanical activation and deactivation of said closing means of said first end, wherein the second end is joined to a mobile coupling member, having an activation extension with an activation edge, inside said second case, shifted by said driving means, said mobile plate being trapped by a pivotable plate from which a knob projects extending form said front wall of the second case, having ribs substantially forming a cam profile in which guide pins of the mobile plate are inserted, facing the pivotable plate; and being rested on a bottom wall of the second case on which second cam profiles are formed by suitable grooves in which the guide pins of the mobile plate are inserted, thus determining a desmodromic system.

2. Device according to claim 1, wherein the first case has a substantially cylindrical shape, coaxial to the catheter section passing through it longitudinally.

3. Device according to claim 1, wherein the closing means comprises a pliers device having one or a pair of claw clutches for throttling said first terminal end of the first tubular member.

4. Device according to claim 3, wherein each claw clutch has a tooth, for throttling and then closing the terminal end of the first tubular member.

5. Device according to claim 4, wherein the closing means comprises a pipe fitted on the first tubular member at the respective terminal end, having, in proximity of the terminal end, two opposed notches leaving uncovered faced areas of the first tubular member, said pliers device having a locking ring, intended to be fitted and blocked on the pipe, said tooth being inserted in the respective notch of the pipe.

6. Device according to claim 3, wherein the claw clutch is composed by resilient leaves, and a pressure on the end thereof in a longitudinal direction being able to bend them, thus opening the terminal end of the first tubular member.

7. Device according to claim 6, wherein the second end is joined to a mobile coupling member inside said second case, shifted by said driving means, the mobile coupling member has an activation extension, with an activation edge, which is provided to interfere and to press said activation ends of the claw clutch.

8. Device (1) according to claim 1, comprising stop means for providing the consent to the detachment between first and second case.

9. Device according to claim 1, wherein the mobile plate comprises catching means to catch a cap of tubular member and/or releasing means to release a cap of tubular member.

10. Device according to claim 9, wherein said catching means and said releasing means comprise cap seats formed in said mobile plate or integral thereto, placed at the sides of the coupling member.

11. Device according to claim 9, wherein said catching means comprises a cap seat having a circumferential tooth to irreversibly catch a cap.

* * * * *

UNITED STATES PATENT AND TRADEMARK OFFICE
CERTIFICATE OF CORRECTION

| | | |
|---|---|---|
| PATENT NO. | : 8,992,508 B2 | Page 1 of 1 |
| APPLICATION NO. | : 12/681257 | |
| DATED | : March 31, 2015 | |
| INVENTOR(S) | : Arduino Arduini, Paolo Cerasoli and Fabio Arrizza | |

It is certified that error appears in the above-identified patent and that said Letters Patent is hereby corrected as shown below:

IN THE CLAIMS

In claim 1, at column 8, line 2, after the word "extending", please delete the word "form" insert thereto --from--.

Signed and Sealed this
Twenty-ninth Day of December, 2015

Michelle K. Lee
*Director of the United States Patent and Trademark Office*